(12) United States Patent
Xie et al.

(10) Patent No.: US 7,462,720 B2
(45) Date of Patent: Dec. 9, 2008

(54) DETERMINATION OF NUCLEIC ACID USING ELECTROCATALYTIC INTERCALATORS

(76) Inventors: Fang Xie, 15/46 Stewart St. Dundas, NSW 2117, Sydney (AU); Hong Xie, BLK212, #11-126, Choa Chu Kang Central, Singapore (SG) 680212; Zhiqiang Gao, 45 Verdr Grove, Singapore (SG) 688577

( * ) Notice: Subject to any disclaimer, the term of this patent is extended or adjusted under 35 U.S.C. 154(b) by 415 days.

(21) Appl. No.: 10/933,023

(22) Filed: Sep. 2, 2004

(65) Prior Publication Data

US 2006/0046254 A1 Mar. 2, 2006

(51) Int. Cl.
*C07F 15/00* (2006.01)
*C12Q 1/68* (2006.01)

(52) U.S. Cl. ............................... 546/10; 435/6; 422/50; 422/68.1; 546/2

(58) Field of Classification Search .................. 546/66, 546/10, 8, 2; 435/6; 422/50, 68.1
See application file for complete search history.

(56) References Cited

U.S. PATENT DOCUMENTS 5,329,046 A * 7/1994 Macholdt et al. ............... 564/8
6,368,807 B2 4/2002 Makino et al.
6,649,350 B2 11/2003 Barton et al.

FOREIGN PATENT DOCUMENTS

WO WO 02/40479 * 5/2002

OTHER PUBLICATIONS

Takagi, M., Threading intercalation to double-stranded DNA and the application to DNA sensing. Electrochemical array technique, *Pure Appl. Chem.*, 73:10, pp. 1573-1577 (2001.).
Takenaka, S., et al., Threading Intercalators as a New DNA Structural Probe, *Bull. Chem. Soc. Jpn.*, 72:327-337 (1999).
First International Electronic Conference on Synthetic Organic Chemistry (ECSOC-1), www.mdpi.org/ecsoc, (Sep. 1-30, 1997).
Popovich, N., Mediated electrochemical detection of nucleic acids for drug discovery and clinical diagnostics, http://www.devicelink.com/ivdt/archive/01/04/001.html.
Popovich, N., et al., New Srategies for Electrochemical Nucleic Acid Detection, *The Electrochemical Society Interface*, pp. 30-34 (2002).

\* cited by examiner

*Primary Examiner*—Charanjit S Aulakh
(74) *Attorney, Agent, or Firm*—Harness, Dickey & Pierce, P.L.C.

(57) ABSTRACT

Compositions and methods for electrochemical detection of nucleic acid are disclosed. The compositions comprise electrocatalytic intercalators that bind to double-stranded nucleic acid and oxidize nucleic acid. Methods of detecting nucleic acid in a sample comprise forming double-stranded nucleic acid that is bound by electrocatalytic intercalators wherein the intercalators catalyze oxidation of the nucleic acid at the surface of an electrode.

34 Claims, 5 Drawing Sheets

DETERMINATION OF NUCLEIC ACID USING ELECTROCATALYTIC INTERCALATORS

FIELD OF THE INVENTION

This application relates generally to biosensors for detection of nucleic acids using electrocatalytic intercalators.

BACKGROUND OF THE INVENTION

Nucleic acid-based biosensors have potential applications that range from genotyping to molecular diagnostics. Fluorescence-based techniques afford high-density nucleic acid arrays for analyzing specific nucleic acid sequences and gene expression. Although widely employed, these arrays require labeling of the target nucleic acid samples. Electrochemical transduction methods have therefore been proposed for ultrasensitive detection of nucleic acid hybridization events. The use of electrochemical techniques instead of fluorescence can allow for simpler and smaller detectors. The ability to directly detect nucleic acid selectively and sensitively has been a major goal of electrochemical research.

SUMMARY OF THE INVENTION

Accordingly, the inventors have succeeded in devising new approaches in biosensors for detecting nucleic acids in a sample. This approach is based on the synthesis and analytical application of novel nucleic acid intercalators for use in ultrasensitive nucleic acid detection.

In various embodiments, the present invention provides a core compound of formula I:

$$L_1\text{-}D\text{-}L_2 \quad (I)$$

wherein D is a divalent cyclic group. $L_1$ and $L_2$ are each independently a linking group comprising an organic amine having from about 3 to about 20 non-hydrogen atoms, an aliphatic amino group, and a nitrogenous moiety.

In further embodiments, the present invention also provides electrocatalytic intercalators comprising the core compound of formula I bonded to a transition metal compound of formula II:

(II)

wherein M is a metallic element that can form a coordinate bond to nitrogen. R and R' are nitrogen-containing organic moieties coordinated to M at their nitrogen atoms. Z is a halogen atom and m is +1, +2, +3, +4, +5, or +6. X is an anion, or combination of anions, that balances m. In a preferred embodiment, the metallic element is ruthenium.

In various further embodiments, the present invention also provides methods for preparing the above-described electrocatalytic intercalators. The method comprises contacting the core compound of formula I with the transition metal compound of formula II so as to form a metal to nitrogen coordinate bond between the core compound and the transition metal compound.

The present invention further provides methods for electrocatalytic detection of nucleic acids utilizing the above-described electrocatalytic intercalator. In various embodiments, the electrocatalytic intercalator is contacted with a complex comprising the target nucleic acid so as to intercalate the electrocatalytic intercalator into the complex.

In still further embodiments, the present invention is also directed to kits comprising electrocatalytic intercalators, as well as, to biosensors that utilize such electrocatalytic intercalators for electrocatalytic detection of nucleic acid.

BRIEF DESCRIPTION OF THE DRAWINGS

The skilled artisan will understand that the drawings, described below, are for illustration purposes only. The drawings are not intended to limit the scope of the present teachings in any way.

FIG. 5 is an illustration of (A) UV-vis spectra of 25 μM PIND-Ru as a function of increasing concentration of salmon sperm DNA (in base pair) of 0 (trace 1), 25 (trace 2), 50 (trace 3), and 100 (trace 4) μM; (B) Fluorescent intercalator displacement titration curve of PIND-Ru against a hairpin oligonucleotide containing the sequence 5'-AATTT-CCCCC-AAATT.

FIG. 6 is an illustration of (A) cyclic voltammograms of 200 nM of poly(T)$_{40}$ hybridized to a non-complementary CP coated electrode (trace 1), and 200 nM of poly(AT)$_{20}$ (trace 2), poly(AG)$_{20}$ (trace 3), and poly(G)$_{40}$ (trace 4) hybridized to their complementary CP coated electrode, respectively; (B) First (trace 1) and fifth (trace 2) potential cycling in PBS of a p53 nucleic acid hybridized biosensor, where potential scan rate is 100 mV/s.

DETAILED DESCRIPTION OF THE INVENTION

In accordance with the present invention, Applicants have discovered novel electrocatalytic intercalators that insert between the base pairs of nucleic acids and catalyze oxidation of nucleotides following electrochemical potentiation. The intercalators of the present invention comprise various moieties that contribute to the electrocatalytic properties of the intercalator. Applicants have discovered that selective incorporation of the electrocatalytic intercalators of the present invention into double-stranded nucleic acid and efficient electrocatalysis provides a general platform for sensitive non-labeling determination or detection of target nucleic acids.

For example, threading intercalators are an important group of compounds that interact reversibly with double-stranded nucleic acids. Threading intercalators share common structural features such as, for example, the presence of planar polyaromatic systems, which bind in insertion between base-pairs of double-stranded DNA. Without being bound by a particular theory, following intercalation of the present electrocatalytic intercalators into double-stranded nucleic acid, electron flow is detected at an electrode wherein the electrocatalytic intercalator oxidizes nucleotides and electrons are transferred from nucleotides to a biosensor/ electrode. Without limiting utility, function, or composition of the present invention, the electrocatalytic intercalator oxidizes nucleotides following electrochemical potentiation. In a catalytic cycle, the intercalator is oxidized by an electrode, which is capable of removing an electron from a nucleotide to form a radical cation that deprotonates and undergoes further reaction. The reaction is thus catalytic and leads to the consumption of nucleic acid through a series of reactions that remove electrons directly from nucleic acids and transfer them to an electrode, resulting in a detectable current.

In one embodiment, the present invention provides core compounds that have structures that correspond to formula (I):

In the formula (I), D represents a divalent cyclic group which may have one or more substituents. The divalent cyclic group preferably comprises a planar cyclic group. Non-limiting examples of divalent cyclic groups include a naphthalene diimide group having two bonding sites at its two nitrogen atoms, an anthracene group having two bonding sites at 2- and 6-positions or 1- and 5-positions (preferably 2- and 6-positions), an anthraquinone group having two bonding sites in the same manner as in the anthracene group, a fluorene group having two bonding sites at 2- and 6-positions, a biphenylene group having two bonding sites at 2- and 6-positions, a phenantholene group having two bonding sites at 2- and 7-positions, and a pyrene group having two bonding sites at 2- and 7-positions. A preferred cyclic group is a naphthalene diimide group having two bondings at the nitrogen atoms. Non-limiting examples of the divalent cyclic group's substituents are halogen atoms (e.g., Chlorine (Cl) or Bromine (Br)), or alkyl groups having 1 to 6 carbon atoms such as methyl, ethyl, or n-propyl.

In a preferred embodiment, D is a nucleic acid intercalator. Intercalators are molecules that can slide between the base pairs of duplex nucleic acid, such as, for example, DNA/DNA or DNA/RNA hybrids. Preferably, the intercalator comprises a naphthalene diimide group. In a preferred embodiment, the intercalator comprises 1,4,5,8-naphthalene tetracarboxylic dianhydride.

In formula (I) described above, $L_1$ and $L_2$ are each independently a linking group comprising an organic amine having from about 3 to about 20 non-hydrogen atoms, an aliphatic amino group, and further comprising a nitrogenous moiety that can provides a metal-to-nitrogen coordinate bond. In a preferred embodiment, the nitrogenous moiety is a heterocyclic ring containing at least one nitrogen atom. Non-limiting examples of suitable nitrogenous moieties include imidazole, benzimidazole, pyrroles, pyrazole, triazoles, benzotriazoles, pyridine, pyridazine, pyrazine, pyrimidine and triazines. One of the nitrogens of the heterocyclic ring can form a coordinate bond to a metal. A preferred nitrogenous moiety is imidazole. When the nitrogenous moiety is a heterocyclic ring, the aliphatic amino group is preferably held on an alkyl group attached to the ring. The alkyl group may be straight chain or branched and contains generally from about 1 to about 20 carbons, preferably from about 2 to about 12 and more preferably from about 3 to about 6 carbon atoms. A preferred linking group is 3-aminopropylimidazole.

In another embodiment, compounds having structures that correspond to the above-described formula (I) are part of an electrocatalytic intercalator. In a preferred embodiment, the electrocatalytic intercalator comprises compound formula (I) bonded to a transition metal compound of formula (II):

where M is a metallic element that forms a coordinate bond to nitrogen. R and R' are nitrogen-containing organic moieties coordinated to M at their nitrogen atoms. Z is a halogen atom and m is +1, +2, +3, +4, +5, or +6. X is an anion, or combination of anions, that balances m.

In formula II, suitable metallic elements for use as M include, for example, ruthenium (Ru), osmium (Os), zinc (Zn), iron (Fe), rhodium (Rh), rhenium (Re), platinum (Pt), scandium (Sc), titanium (Ti), vanadium (V), cadmium (Cd), magnesium (Mg), copper (Cu), cobalt (Co), palladium (Pd), chromium (Cr), manganese (Mn), nickel (Ni), Molybdenum (Mo), tungsten (W), iridium (Ir) and mixtures thereof. In a preferred embodiment, the metallic element M is the transition metal ruthenium (Ru).

R and R' of formula II can be the same or different and are coordinated to the metallic element at their nitrogen atoms. R, R', or both can be, for example, 2,2'-bipyridyl; 2,2'-bipyridyl substituted with one or more substituents selected from the group consisting of C1-C4 alkyl, phenyl and phenyl substituted with one or more C1-C4 alkyl groups; 1,10-phenanthrolinyl and 1,10-phenanthrolinyl substituted with one or more substituents selected from the group consisting of C1-C4 alkyl, phenyl and phenyl substituted with one or C1-C4 alkyl groups. Preferably, at least one of R and R' is 2,2'-bipyridyl.

In another embodiment, at least one and preferably both of R and R' is a 2,2'-bipyridyl or 1,10-phenanthrolinyl, either of which can be optionally substituted. When the bipyridyl or phenanthrolinyl is substituted, the substituents are preferably selected from the group consisting of among C1 to C4 alkyl, phenyl, and phenyl substituted further with C1-C4 alkyl, more preferably C1-C2 alkyl groups. The substituted bipyridyl and phenathrolinyl liganding groups can be monosubstituted, disubstituted, or higher substituted. In various embodiments, disubstituted liganding groups, including for example, 4,4'-disubstituted-2,2'-bipyridyl, 5,5'-disubstituted-2,2'-bipyridyl, 1,10-phenanthrolinyl, 4,7-disubstituted-1,10-phenanthrolinyl and 5,6-disubstituted-1,10-phenanthrolinyl, can be used.

When only one of R and R' is a bipyridyl or phenanthrolinyl or one of the optionally substituted groups discussed above, the other is preferably selected from aliphatic ligands containing two nitrogen atoms capable of forming coordinate bonds with the metal M. Non-limiting examples include 1,3-propanediamine, 1,4-butanediamine and derivatives of either, where the derivatives are based on 1,3-propanediamine or 1,4-butanediamine skeletons optionally substituted with alkyl, aryl, or other groups that do not interfere with coordinate bonding of the nitrogens to the metal M or with the electrochemical activity of the complex.

In formula II, Z is a halogen atom. In a preferred embodiment Z is chlorine or bromine, and more preferably chlorine. The superscript m is +1, +2, +3, +4, +5, or +6, depending on the oxidation state of M. In a preferred embodiment, for example, when M is ruthenium in the +4 oxidation state, Z is chlorine and m is +3. X is an anion, or combination of anions, that balances the formal charge m of the cation. For example, X can be, without limitation, chloride, bromide, iodide, fluoride, tetrafluoroborate, perchlorate, nitrate, sulfate, carbonate, or sulfite.

In a preferred embodiment, the electrocatalytic intercalator of the present invention comprises the compound of formula (I) bonded to the compound of formula (II) where D is 1,4,5, 8-naphthalene tetracarboxylic dianhydride, $L_1$ and $L_2$ are each 3-aminopropylimidazole, M is ruthenium, R and R' are each 2,2'-bipyridyl, and Z is chlorine. More preferably the electrocatalytic intercalator of the present invention comprises the formula:

The present invention also provides for methods of preparing the above-described electrocatalytic intercalators. In a preferred method of the present invention, the electrocatalytic intercalator is prepared by ligand exchange between the core compound of general formula (I) and a transition metal compound of general formula (II). The transition metal compounds described herein comprise filler ligands Z that help form a stable complex with the metal and are displaceable by the linking group, $L_1$ or $L_2$, under the conditions of the ligand exchange. Preferred linking groups comprise a nitrogenous moiety that provides a metal-to-nitrogen coordinate bond to the metal. In a preferred embodiment, the metal is ruthenium, Z is chlorine, and the linking group is 3-aminopropylimidazole.

The electrocatalytic intercalators of the present invention may be used for detecting target nucleic acid in a sample. In a non-limiting example, a complex comprising the nucleic acid and the electrocatalytic intercalator is formed at the surface of a solid support, such as an electrode and electron transfer is detected. In accordance with the present invention, the electrocatalytic intercalator inserts between base-pairs of double-stranded nucleic acid comprising the target nucleic acid hybridized to a complementary probe molecule. Without limiting the mechanism, function or utility of present invention, such methods take advantage of electrochemical oxidation of nucleotides. The electrocatalytic intercalators can oxidize nucleotides, preferably guanines, upon intercalation into double-stranded nucleic acid and upon appropriate electrochemical potentiation. Without being bound by a particular theory, in a catalytic cycle, the intercalator is oxidized by an electrode, which is capable of removing an electron from a nucleotide to form a radical cation that deprotonates and undergoes further reaction. The reaction is catalytic and leads to the consumption of nucleic acid through a series of reactions that remove electrons directly from nucleic acids and transfers them to an electrode, resulting in a detectable current.

In one embodiment, a complex comprising the target nucleic acid and the electrocatalytic intercalators is formed at the surface of an electrode by virtue of hybridization of the target nucleic acid to a probe that either is immobilized on the electrode surface or is able to bind to the electrode surface. Suitable probes can comprise nucleic acids comprising a single-stranded region complementary to a specific sequence of the target nucleic acid. The target nucleic acid to be detected can comprise nucleic acid, which may be single stranded or double stranded, as specified, or contain portions of both double stranded or single stranded sequence. Where the target nucleic acid comprises only double stranded nucleic acid, it is understood that denaturation is required prior to hybridization of the target nucleic acid to the complementary probe.

The target nucleic acid can be DNA (either genomic or cDNA), RNA, or a hybrid, where the nucleic acid contains any combination of deoxyribo- and ribo-nucleotides and any combination of bases, including for example, uracil, adenine, thymine, cytosine, guanine, inosine, xathanine, hypoxathanine, and the like. The binding of target nucleic acid to probe can be, for example, by hybridization.

Generally, the probe can comprise, for example, oligonucleotides, including DNA, mRNA, rRNA, tRNA, peptide nucleic acids (PNAs), or expressed sequence tags (ESTs). The probe can be obtained from DNA or its fragment, which may be obtained by extraction from a living body, cleavage by restriction enzyme, separation by electrophoresis, and denaturation by heat-treatment or alkaline-treatment. The probe can also be chemically synthesized. Also the probe can be synthesized using an alternate base that would substitute for guanine (i.e., a base that, like guanine, has a greater binding affinity for cytosine than do other bases in a nucleic acid duplex) in the probe strand but would not be oxidized by the electrocatalytic intercalator under the applicable reaction conditions. Examples of such alternate bases are inosine and 7-deaza-guanine.

Suitable bases for preparing the probe may be selected from naturally occurring or normally occurring or "synthetic" nucleotide bases. Naturally occurring nucleotide bases may be, for example, adenine, cytosine, guanine, uracil, and thymine. Probes may be also be prepared from naturally occurring or "synthetic" nucleotide bases such as 7-deaza-guanine, 8-oxo-guanine, 6-mercaptoguanine, 4-acetylcytidine, 5-(carboxyhydroxyethyl)uridine, 2'-O-methylcytidine, 5-carboxymethylanino-methyl-2-thioridine, 5-carboxymethylaminomethyluridine, dihydrouridine, 2'-O-methylpseudouridine, β-D-galactosylqueosine, 2'-O-methylguanosine, inosine, N6-isopentenyladenosine, 1-methyladenosine, 1-methylpseeudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2- thiouridine, β-D-mannosylqueosine, 5-methoxycarbonylmethyluridine, 5-methoxyuridine, 2-methylthio-N-6-isopentenyladenosine, N-((9-β-D-ribofuranosyl-2-methylthiopurine-6-yl)carbamoyl)threonine, N-((9-β-D-ribofuranosylpurine-6-yl)N-methylcarbamoyl)threonine, uridine-5-oxyacetic acid methylester, uridine-5-oxyacetic acid, wybutoxosine, pseudouridine, queosine, 2-thiocytidine, 5-methyl-2-thiouridine, 2-thiouridine, 2-thiouridine, 5-methylurdine, N-((9-β-Dribofuranosylpurine-6-yl)carbamoyl)threonine, 2'-O-methyl-5-methyluridine,2'-O-methyluridine, wybutosine, and 3-(3-amino-3-carboxypropyl)uridine. Any oligonucleotide backbone may be employed, including DNA, RNA, modified sugars such as carbocycles, and sugars containing 2' substitutions such as fluoro and methoxy. The oligonucleotides may be oligonucleotides wherein at least one, or all, of the internucleotide bridging phosphate residues are modified phosphates, such as methyl phosphonates, methyl phosphonothioates, phosphoromorpholidates, phosphoropiperazidates and phosphoramidates (for example, every other one of the internucleotide bridging phosphate residues may be modified as described).

The oligonucleotide may be a "peptide nucleic acid" such as described in P. Nielsen et al., Science 254, 1497-1500 (1991), which is hereby incorporated herein by reference. The only requirement is that the oligonucleotide probe should possess a sequence at least a portion of which is capable of binding to a known portion of the sequence of the DNA sample. It may be desirable in some applications to contact the target nucleic acid sample with a number of oligonucleotide probes having different base sequences (e.g., where there are two or more target nucleic acids in the sample, or where a single target nucleic acid is hybridized to two or more probes in a "sandwich" assay).

The probe molecule can be immobilized onto an electrode. In a preferred embodiment, probe is attached to gold electrodes. However, one skilled in the art would understand that the probe can be immobilized to the electrode by a number of techniques known in the art. Employing literature procedures, a variety of techniques are available and known to those skilled in the art for immobilizing probes onto the surface of electrodes for use in accordance with the present invention.

In a non-limiting example, a thiol group can be attached to 5'- or 3'-terminal (5'-terminal is preferred) of the probe molecule, such as, oligonucleotide or polynucleotide, and the attached thiol coordinates a gold atoms of the electrode. The method for incorporating a thiol group to the DNA is described in M. Maeda et al., Chem. Lett., 1805-1806 (1994) and A. Connolly, Nucleic Acids Res., 13, 4484 (1985), which is hereby incorporated herein by reference. In the fixation process, the probe molecule having thiol terminal is dropped onto the gold electrode, and then the desired probe molecule is fixed on the electrode after allowing it to stand for a few hours at a low temperature.

In another non-limiting example, such as the use of a glassy carbon electrode, the electrode is oxidized by potassium permanganate to produce carboxyl groups on the surface of the electrode. On the surface having carboxyl groups is dropped the probe molecule having thiol terminal, so that an amide bonding is formed to fix the probe molecule onto the surface of the glassy carbon electrode. Details of this method are described in K. M. Millan et al., Analytical Chemistry, 65, 2317-2323 (1993), which is hereby incorporated herein by reference.

Recognition pairs can also be used to attach probe to electrode. In this regard, the probe can be modified to comprise a first member of a recognition pair where the electrode surface is coated with a second member. Accordingly, a double-stranded nucleic acid comprising probe/target nucleic acid hybrid can form at the surface of the electrode via interaction of the first and second members of the recognition pairs. Recognition pairs and their attachments to various molecules are known in the art. In a non-limiting example, a recognition pair consists of biotin and avidin.

Hybridization of target nucleic acid to probe can be carried out prior to addition of the intercalator or in the presence of the intercalator, which is preferably used in a concentration of several nM to several mM. The target nucleic acid sample may be contacted with the probe in any suitable manner known to those skilled in the art. For example, the target sample may be solubilized in solution, and contacted with the probe by solubilizing the probe in solution with the target sample under conditions which permit hybridization. Suitable conditions are well known to those skilled in the art and include various salt concentration conditions. Alternatively, the target sample may be solubilized in solution with the probe immobilized on a solid support, whereby the target sample may be contacted with the probe by immersing the solid support having the oligonucleotide probe immobilized thereon in the solution containing the target sample. Hybridization of the target nucleic acid to the probe molecule is determined upon application of an electric potential to the electrode and detection of current.

The electrocatalytic intercalators of the present invention can also be employable for detecting target nucleic acid fragment samples that are partly complementary to the probe molecules. Such fragment samples are generally referred to as "mis-match fragment". The detection of the mis-match fragment can be performed by comparing the strength of the peak current obtained in the detection of the possibly mis-matched target nucleic acid fragment with the strength of the corresponding peak current obtained in the detection of a fully complementary target nucleic acid fragment (i.e., full-match fragment).

The catalytic cycles involving oxidation and reduction may be detected according to any suitable means known to those skilled in the art. The detection of the electronic signal associated with the oxidation and reduction reaction permits the determination of the presence or absence of hybridized probe/target nucleic acid. The step of measuring the reaction rate may be carried out by any suitable means. For example, the relative reaction rate may be determined by comparing the current as a function of scan rate, probe concentration, target concentration, mediator, buffer, temperature, and/or electrochemical method.

The oxidation-reduction reaction rate may be measured according to suitable means known to those skilled in the art. Typically, the oxidation-reduction reaction rate is measured by measuring the electronic signal associated with the occurrence of the oxidation-reduction reaction. For example, the electronic signal associated with the oxidation-reduction reaction may be measured by providing a suitable apparatus in electronic communication with the detection electrode. A suitable apparatus will be capable of measuring the electronic signal which is generated so as to provide a measurement of the oxidation-reduction reaction rate of the reaction of the hybridized probe/target nucleic acid and the electrocatalytic intercalator. The electronic signal may be characteristic of any electrochemical method, including cyclic voltammetry, normal pulse voltammetry, chronoamperometry, and square-wave voltammetry, with cyclic voltammetry being the currently preferred form.

In preferred embodiments, the methods are used in genetic diagnosis. For example, oligonucleotide probes can be used for determining target analyte sequences such as the gene for p53, which is a gene associated with a variety of cancers. Other non-limiting examples include the gene for nonpolyposis colon cancer, the BRCA1 breast cancer gene, the Apo E4 gene that indicates a greater risk of Alzheimer's disease allowing for easy presymptomatic screening of patients, mutations in the cystic fibrosis gene, or any of the others well known in the art.

In various other embodiments, viral and bacterial detection can be carried out using the electrocatalytic intercalators of the invention. In this embodiment, probes are designed to detect target sequences from a variety of bacteria and viruses. The methods disclosed herein allow for direct screening of clinical samples to detect, for example, HIV nucleic acid sequences. In addition, this allows direct monitoring of circulating virus within a patient as an improved method of assessing the efficacy of anti-viral therapies. Similarly, viruses associated with leukemia, HTLV-1 and HTLV-II, may be detected in this way. Bacterial infections such as tuberculosis may also be detected.

In other embodiments, probes for toxic bacteria in the screening of, for example water and food samples. For example, samples may be treated to lyse the bacteria to release its nucleic acid and then probes designed to recognize bacterial strains, including, but not limited to, such pathogenic strains as, *Salmonella, Campylobacter, Vibrio cholerae*, enterotoxic strains of *E. coli* and Legionnaire's disease bacteria. Similarly, bioremediation strategies may be evaluated using the compositions of the invention.

In other embodiments, the probes can be used for forensics where DNA fingerprinting is used to match crime-scene target nucleic acid such as DNA against samples taken from victims and suspects.

The source of target nucleic acid can include, for example, humans, animals, plants, or environment.

In other embodiments, the present invention is also directed to kits comprising electrocatalytic intercalators. The kits can further comprise probes, such as those described herein, which can recognize and bind to the target nucleic acid to be detected.

In various other embodiments, the present invention is further directed to a biosensor that utilizes the electrocatalytic intercalators described herein. The biosensor may comprise an apparatus or be used in a system that includes the necessary components for detecting and measuring a signal produced by one or more electrocatalytic intercalators. An apparatus can comprise integrated circuits including a biosensor array combined with a power supply and a detector. Such integrated circuits are known to those of skill in the art. Systems including the biosensor array may additionally include means for measuring an electrochemical signal after a potential is applied across a working electrode.

The methods and apparatus described herein utilize laboratory techniques well known to skilled artisans and can be found in laboratory manuals such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; and Harlow, E., Using Antibodies: A Laboratory Manual, Cold Spring Harbor Laboratory Press, Cold Spring Harbor, N.Y., 1999.

The methods and apparatus described herein utilize laboratory techniques well known to skilled artisans and can be found in laboratory manuals such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; and Harlow, E., Using Antibodies: A Laboratory Manual, Cold Spring Harbor Laboratory Press, Cold Spring Harbor, N.Y., 1999.

The headings (such as "Background of the Invention" and "Summary of the Invention") used herein are intended only for general organization of topics within the disclosure of the invention and are not intended to limit the disclosure of the invention or any aspect thereof. In particular, subject matter disclosed in the "Background of the Invention" may include aspects of technology within the scope of the invention and may not constitute a recitation of prior art. Subject matter disclosed in the "Summary of the Invention" is not an exhaustive or complete disclosure of the entire scope of the invention or any embodiments thereof.

The citation of references herein does not constitute an admission that those references are prior art or have any relevance to the patentability of the invention disclosed herein. All references cited in the specification are hereby incorporated by reference in their entirety.

The description and specific examples, while indicating embodiments of the invention, are intended for purposes of illustration only and are not intended to limit the scope of the invention. Moreover, recitation of multiple embodiments having stated features is not intended to exclude other embodiments having additional features, or other embodiments incorporating different combinations of the stated features. Specific Examples are provided for illustrative purposes of how to make, use and practice the compositions and methods of this invention and, unless explicitly stated otherwise, are not intended to be a representation that given embodiments of this invention have, or have not, been made or tested.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the invention.

As used herein, the word "include," and its variants, is intended to be non-limiting, such that recitation of items in a list is not to the exclusion of other like items that may also be useful in the materials, compositions, devices and methods of this invention.

In the following description the terms "determination" or "detection" will be used to denote both qualitative and quantitative determination or detection of nucleic acid in a sample. Where, for example, the method and system defined below are used for determining or detecting a nucleic acid in a medium, this is meant to denote determining the presence of an nucleic acid in the medium and optionally its concentration. Accordingly, the phrase "determining the presence or absence of" is intended to include both qualitatively determining and quantitatively determining the presence or absence of the detected event (e.g., DNA hybridization, RNA hybridization, detecting target nucleic acid, etc.).

As used herein, the term "intercalator" is meant to denote planar aromatic or heteroaromatic moieties that are capable of insertion and/or stacking between the base pairs of nucleic acids.

As used herein, the term "threading intercalator" is meant to denote an intercalator bearing substituents or side chains.

As used herein, the term "electrocatalytic intercalator" is meant to denote an intercalator that can be oxidized by an electrode and can oxidize a nucleotide following electrochemical potentiation.

As used herein, the term "nucleic acid" refers to any nucleic acid, including both DNA and RNA. Nucleic acids of the present invention are typically polynucleic acids; that is, polymers of individual nucleotides that are covalently joined by 3', 5' phosphodiester bonds. While the methods and apparatus of the present invention are sometimes explained with respect to DNA herein, this is for purposes of clarity, and it is to be understood that the methods and apparatus of the instant invention may be applied to other nucleic acids such as RNA.

As used herein, the term "complementary nucleic acid" refers to any nucleic acid, including oligonucleotide probes, that specifically binds to another nucleic acid to form a hybridized nucleic acid.

As used herein, the terms "hybridized" or "hybridization" are meant to denote at least two nucleic acid strands associated with each other which may or may not be fully base-paired.

As used herein, the terms "denaturing" or "denaturation" are meant to denote the process by which strands of oligonucleotide duplexes are no longer base-paired by hydrogen bonding and are separated into single-stranded molecules. Methods of denaturation are well known to those skilled in the art and include thermal denaturation and alkaline denaturation.

As used herein, the term "electrode" is meant to denote an electric conductor that conducts a current in and out of an electrically conducting medium. The two electrodes, the anode and the cathode, receive and emit electrons, respectively. An electrode is used generally to describe the conductor. In the present invention, an electrode may also be a microarray, consisting of a number of separately addressable electrodes, or an ultramicroelectrode.

As used herein, the term "nucleoside" is meant to denote a nitrogenous heterocyclic base linked to a pentose sugar, either a ribose, deoxyribose, or derivatives or analogs thereof. The term "nucleotide" relates to a phosphoric acid ester of a nucleoside comprising a nitrogenous heterocyclic base, a pentose sugar, and one or more phosphate or other backbone forming groups; it is the monomeric unit of an oligonucleotide. Nucleotide units may include the common bases such as guanine (G), adenine (A), cytosine (C), thymine (T), or derivatives thereof. The pentose sugar may be deoxyribose, ribose, or groups that substitute therefore.

As used herein, the terms "nucleotide analog", "modified base", "base analog", or "modified nucleoside" are meant to denote moieties that function similarly to their naturally occurring counterparts but have been structurally modified.

As used herein, the terms "oligonucleotide" or "nucleotide sequence" are meant to denote a plurality of joined nucleotide units formed in a specific sequence from naturally occurring heterocyclic bases and pentofuranosyl equivalent groups joined through phosphorodiester or other backbone forming groups.

As used herein, the term "oligonucleotide analogs" or "modified oligonucleotides" are meant to denote compositions that function similarly to natural oligonucleotides but have non-naturally occurring portions. Oligonucleotide analogs or modified oligonucleotides may have altered sugar moieties, altered bases, both altered sugars and bases or altered inter-sugar linkages, which are known for use in the art.

As used herein, the term "biosensor" is meant to denote an apparatus or system that comprises the necessary components for detecting or measuring a signal produced by movement of electrons produced in an oxidation or reduction reaction. The term "biosensor" includes devices for determining the concentration of substances and other parameters of biological interest even where a biological system is not directly utilized.

EXAMPLES

The following examples are intended to be illustrative and are not intended to limit the scope of the invention.

Example 1

This example illustrates the synthesis of an electrocatalytic intercalator (N,N'-bis[1(3-propyl)-imidazole]-1,4,5,8-naphthalene diimide (PIND) grafted with Ru(bpy)$_2$Cl$_2$ ("PIND-Ru")).

The synthesis of PIND-Ru is outlined as follows:

-continued

PIND is prepared following a general procedure for the synthesis of 1,4,5,8-naphthalene tetracarboxylic dianhydride (ND). 0.30 g of 1,4,5,8-naphthalene tetracarboxylic dianhydride is slowly added to a magnetically stirred mixture of 3.0 ml of 3-aminopropylimidizole (AI) and 3.0 ml of tetrahydrofuran. The rate of addition is controlled so that there is little clogging. The reaction mixture is refluxed for 24 h and then cooled to room temperature. Next, the reaction is dispersed in 10 ml of acetone/water (3/1) mixture and then poured into 500 ml of rapidly stirred anhydrous ether to precipitate the compound. The precipitate is collected by suction filtration through a fine fritted funnel and washed briefly with ethanol. Purification is performed by crystallization from chloroform/ethanol (1/1 by volume) and dried under vacuum at 40° C. overnight to give 0.46 g of yellow crystals (yield 85%).

PIND-Ru is synthesized in a single-step ligand-exchange reaction. To a solution of $Ru(bpy)_2Cl_2$ (0.52 mmol) in 8.0 ml fresh-distilled ethylene glycol is added PIND (0.25 mmol) in small portions over 10 min and the result mixture is refluxed for 30-40 min. The completion of the ligand-exchange reaction is monitored by cyclic voltammetry. The purple reaction mixture is then poured slowly into 100 ml of rapid stirred ethanol saturated with KCl. The precipitate is collected by suction filtration through a fine fritted funnel. The crude product is washed with PBS, dissolved in 3.0-5.0 ml of ethanol and precipitated again from KCl saturated ethanol. The precipitate is further purified by crystallization from ethanol giving the pure product in 78% yield. The product shows a single pair of reversible redox waves at a gold electrode with an $E_{1/2}$ of 0.63 V in PBS. To ensure a complete double ligand-exchange at the two imidazole termini of PIND, slight excess of $Ru(bpy)_2$ (10-15%) is required.

Mass spectrometric experiments is performed with a Finnigan/MAT LCQ Mass Spectrometer (ThermoFinnigan, San Jose, Calif.). All spectra is recorded at room temperature unless otherwise noted.

Figure 1:
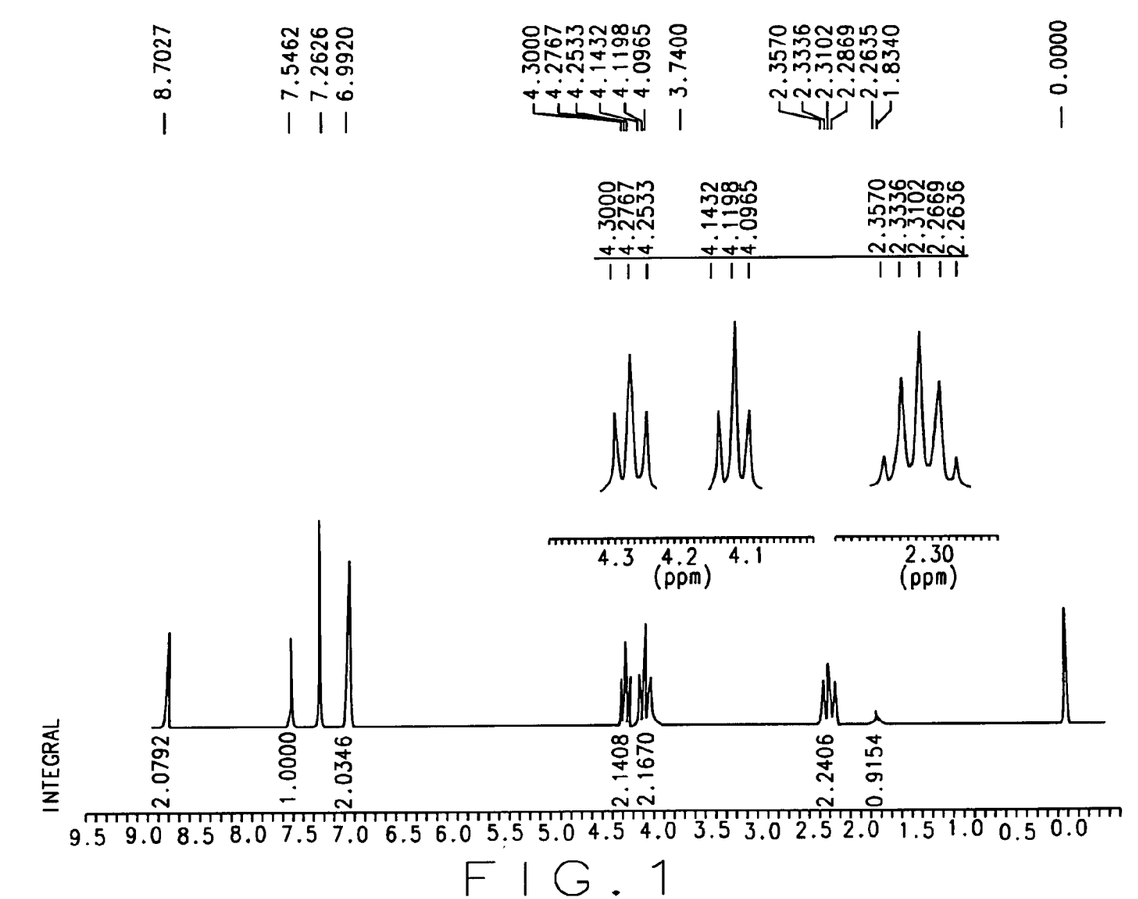
FIG. 1 is an illustration of Proton Nuclear Magnetic Resonance ($^1$H NMR) Spectroscopy (300 MHz) of PIND in $CDCl_3$.

Proton Nuclear Magnetic Resonance ($^1$H NMR) Spectroscopy (300 MHz $CDCl_3$) δ 8.76 (4H), 7.54 (2H), 7.26 (2H), 4.27 (4H), 4.12(4H), 2.31 (4H) and 1.83 9(2H) (FIG. 1).

Figure 2:
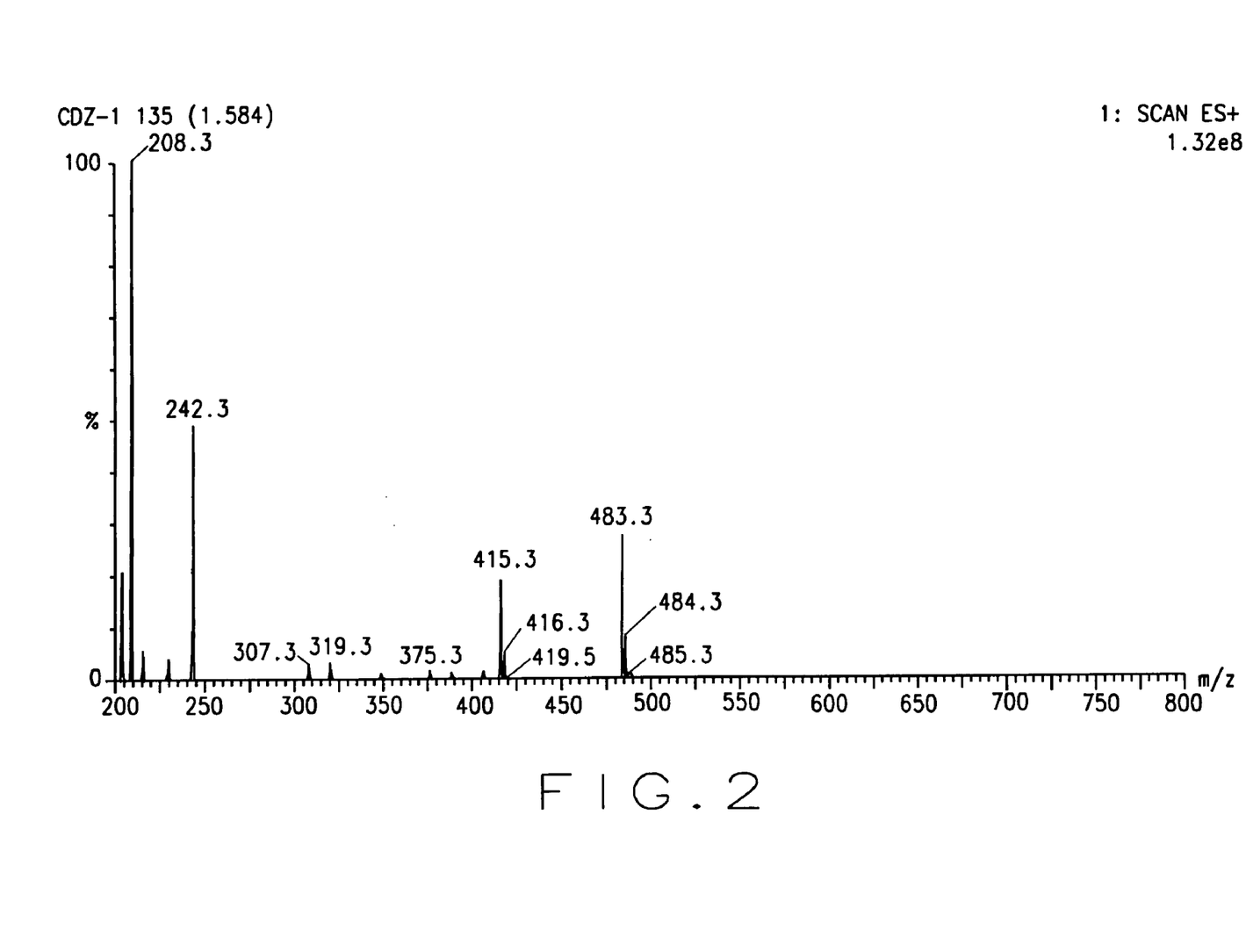
FIG. 2 is an illustration of mass spectrometric tests on PIND using electron-spray ionization mode.

Mass spectrometric tests on PIND using electron-spray ionization mass spectrometry (ESI-MS) shows predominant peaks at m/z 483.3 and 242.3, corresponding to PIND+H$^+$, (and (PIND+2H$^+$)/2 (FIG. 2), which are in good agreement with the molecular weights of the desired compounds. Since mono-grafted PIND is not observed in the ESI-MS spectrum, we can rule out any incomplete grafting of PIND.

Example 2

This example illustrates the formation and electrochemical properties of the electroactive PIND-RU intercalator using cyclic voltammetry.

Figure 3:
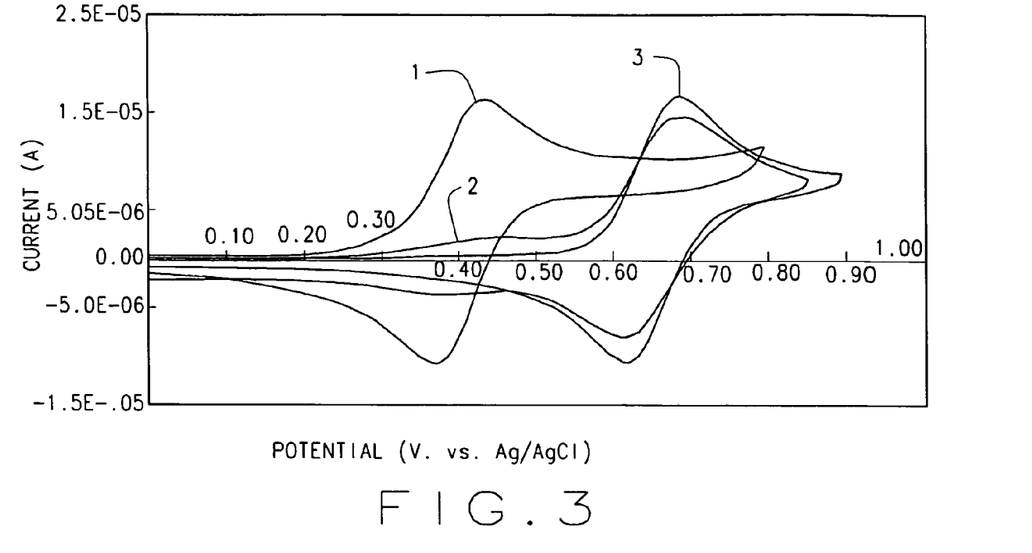
FIG. 3 is an illustration of cyclic voltammograms of $Ru(bpy)_2Cl_2$ (trace 1), $Ru(bpy)_2Cl_2$ (trace 2) after 30 min of refluxing with PIND in ethylene glycol, and purified PIND-Ru (trace 3), where supporting electrolyte for (trace 3) is PBS and potential scan rate is 100 mV/s.

During reflux in the ethylene glycol, cyclic voltammetric tests are conducted every 5 min. FIG. 3 shows two typical voltammograms obtained in the first 30 min. As can be seen in trace 1 in FIG. 3, before adding PIND to $Ru(bpy)_2Cl_2$, one pair of reversible voltammetric peaks centered at 0.40 V are obtained, corresponding to the well-known redox process of $Ru(bpy)_2Cl_2$. Upon adding PIND, a new pair of voltammetric peaks appear at 0.63 V, indicating the formation of PIND-Ru (FIG. 3, trace 2). Both electron transfer processes are clearly resolved and have all the characteristics of reversible processes, except the slightly larger peak-to-peak potential separation which is mainly due to a higher iR drop of the reaction medium. The intensity of the voltammetric peak at 0.63 V increases gradually with reaction time. Simultaneously, those at 0.40 V diminish gradually. Both of the redox pairs reach a steady-state after 30-40 min of refluxing. The minute voltammetric peaks at 0.40 V are indicative of the excess amount of $Ru(bpy)_2Cl_2$. After separation and purification, voltammetric tests of the thus purified PIND-Ru show only one pair of voltammetric peaks implying that the purification process is very effective (FIG. 3, trace 3).

Figure 4:
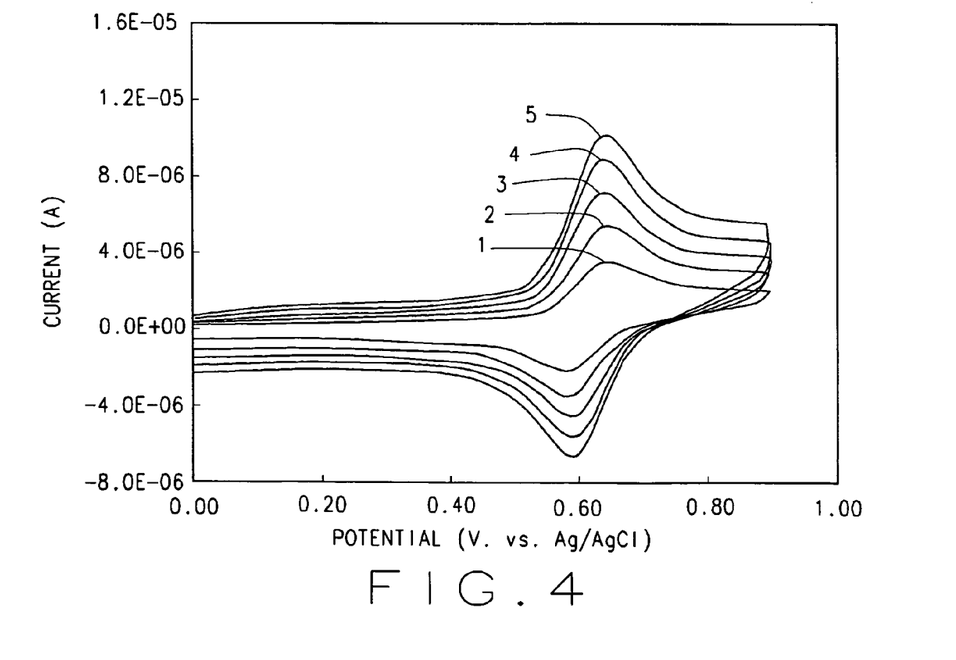
FIG. 4 is an illustration of cyclic voltammograms of the purified PIND-Ru in PBS where potential scan rate from the innermost to the outmost voltammograms were 100 (trace 1), 200 (trace 2), 300 (trace 3), 400 (trace 4) and 500 (trace 5) mV/s.

As illustrated in trace 3 in FIG. 3, PIND-Ru exhibits exactly as expected for a highly reversible redox couple in solution. Little change is observed after numerous repetitive potential cycling between 0.0 and +0.90V, revealing good stability of PIND-Ru in solution. At slow scan rates, <500 mV/s, a typical diffusion-controlled voltammogram is recorded as expected for a one-electron exchange system exhibiting an ideal Nemstian behavior: the peak current is proportional to the square root of the potential scan rate, the peak-to-peak potential separation is very close to the theoretical value of 59 mV and potential scan rate independent (FIG. 4). Such results ascertain that all of the ruthenium redox centers are allowed to reach the electrode surface and proceed to reversible heterogeneous electron transfer.

Example 3

This example illustrates the interaction of PIND-Ru with ds-DNA as determined by UV-vis spectrophotometry of PIND-Ru.

Figure 5A:
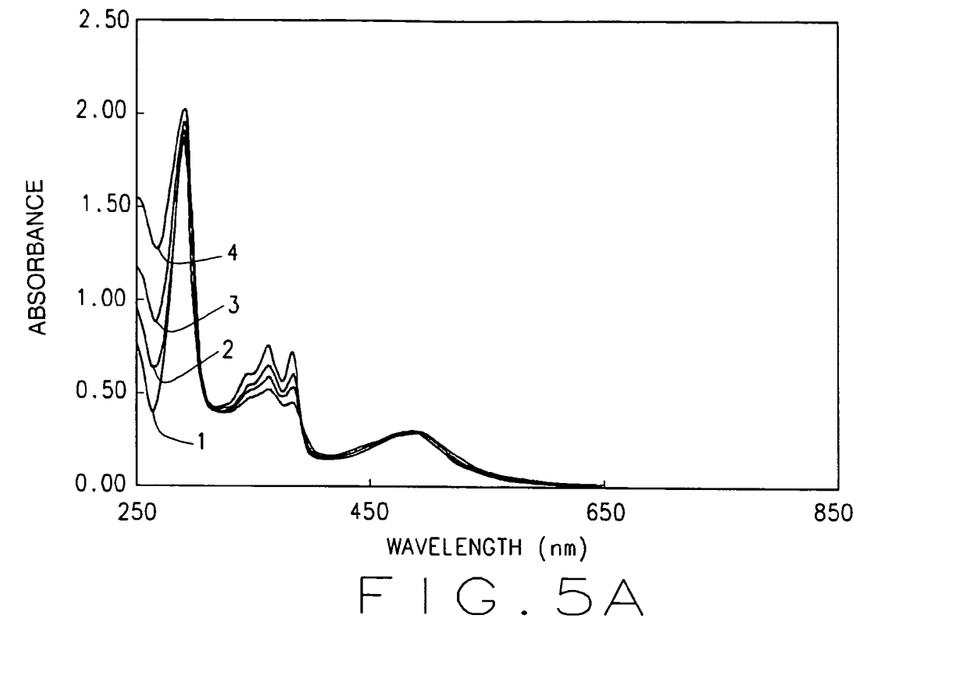

The mode of interaction of PIND-Ru with ds-DNA is determined by UV-vis spectrophotometry of PIND-Ru in the presence of increasing amounts of salmon sperm DNA was investigated (FIG. 5A). UV-visible spectra is recorded on an Agilent 8453 UV-visible spectrophotometer. In the UV-vis spectrophotometry, signatures of intercalative binding, where the fused planar aromatic ring system of a threading intercalator inserts itself between the base pairs of ds-DNA, are hypochromism and red shifts. As shown in FIG. 5A, addition of DNA to PIND-Ru at a DNA base pair/PIND-Ru ratio of 4.0 results in a 40% decrease and a 2-nm-red-shift of the ND absorbance band at 366 and 387 nm. Similar phenomena were previously observed with naphthalene diimide (ND) having aliphatic tertiary amine side chains. The ND absorbance band hypochromism reaches a plateau at the DNA base pair/PIND-Ru ratio>4.0, and a constant hypochromism is observed, indicating that binding of PIND-Ru to ds-DNA takes place by preferential intercalation of the ND.

Figure 5B:
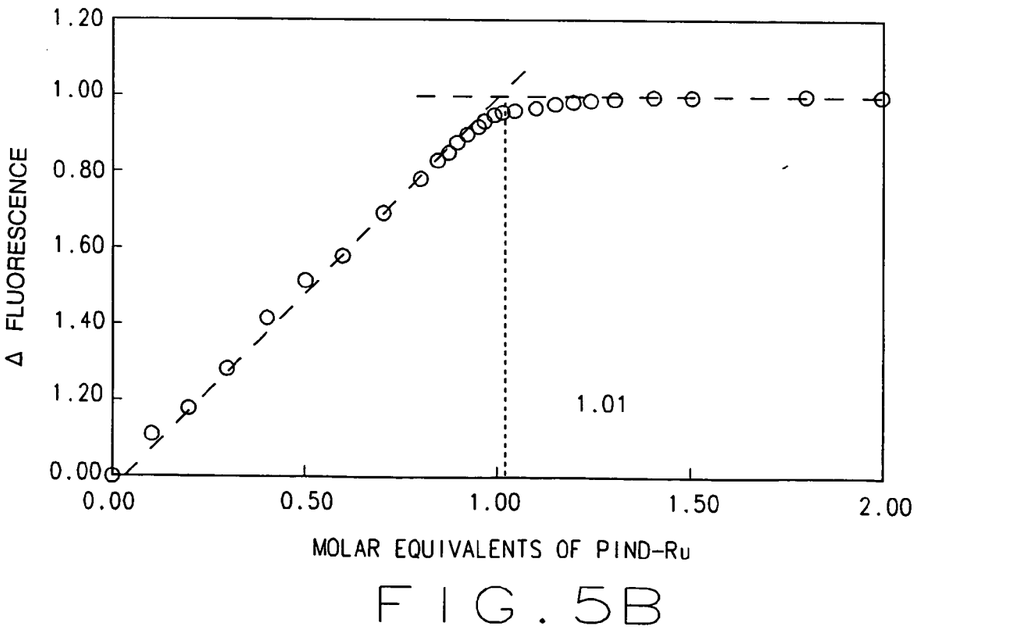

The stability of the intercalation is estimated through a competition experiment using short hairpin oligonucleotides similar to that proposed by Boger. A plot of the change in fluorescence versus equivalents of PIND-Ru provides a titration curve from which the stoichiometry of 1:1 is determined (FIG. 5B). The stability constant, determined through the competition experiment, is found to be $3.0 \times 10^7$, corresponding to approximately a 75-fold enhancement over ND. A plausible explanation for the stability constant enhancement would be that after the ND group has intercalated with ds-DNA, the two cationic Ru(bpy)$_2$Cl groups in PIND-Ru form ion-pairs with phosphates on each side of the ds-DNA, making ND more tightly fixed in between the base pairs of ds-DNA.

Example 4

This example illustrates the application of PIND-RU in DNA biosensors.

The preparation and pretreatment of gold electrode are as previously described in Xie et al., *Anal. Chem.* 76: 1611-1617 (2004); Xie et. al. *Nucelic Acids Res.* 32, e15 (2004); Xie et. al. *Anal. Chem.* 76:4023-4029 (2004); and Gao et al. *Synth. Met.* 75: 5-10 (1995), all of which are hereby incorporated herein by reference. Briefly, prior to capture probe (CP) adsorption, a gold electrode is exposed to oxygen plasma for 5-10 min and then immersed immediately in absolute ethanol for 20 min to reduce the oxide layer. CP monolayer is adsorbed by immersing the gold electrode in a PBS solution of 100 µg/ml CP for 16-24 h. After adsorption, the electrodes are copiously rinsed with PBS and soaked in PBS for 20 min, rinsed again, and blown dry with a stream of air. The surface density of CP, assessed electrochemically by the use of cationic redox probe according to the procedure proposed by steel, is found to be in the range of $1.13$-$1.30 \times 10^{-11}$ mol/cm$^2$. To minimize non-DNA related PIND-Ru uptake and improve the quality and stability of the CP monolayer, the CP-coated gold electrode is immersed in an ethanolic solution of 2.0 mg/ml 1-mercaptododecane (MD) for 4-6 h. Unreacted MD molecules are rinsed off and the electrode is washed by immersion in a stirred ethanol for 10 min and followed by thorough rinsing with ethanol and water. The electrode is ready after air-dry.

The hybridization of a target DNA and its electrochemical detection is carried out in three steps. First, a 2.5 µl aliquot of hybridization solution containing the target DNA is uniformly spread onto the electrode and the electrode is placed in a moisture saturated environmental chamber maintained at 60° C. (low stringency 27° C. below the salt-adjusted melting temperature) 30 min. It is then rinsed thoroughly with a blank hybridization solution at 60° C. and incubated at 35° C. for 10 min with a 5.0 µl aliquot of 100 µg/ml of PIND-Ru in the hybridization solution. PIND-Ru is attached to the hybridized target DNA via threading intercalation. After the electrode is air-cooled and held at room temperature for 10 min, a thorough rinsing with NaCl-saturated phosphate buffer (pH7.4) containing 10% ethanol is conducted. The electrocatalytic oxidation current is measured voltammetrically. At low DNA concentrations, smoothing is applied after each measurement to remove random noise and electromagnetic interference.

Electrochemical experiments are carried out using a CH Instruments model 660A electrochemical workstation coupled with a low current module (CH Instruments, Austin, Tex.). The three-electrode system consists of a 3.0-mm-diameter gold working electrode, a nonleak-miniature Ag/AgCl reference electrode (Cypress Systems, Lawrence, Kans.) and a platinum wire counter electrode. To avoid the spreading of the sample droplet beyond the 3.0-mm diameter working area, a patterned hydrophobic film is applied to the gold electrode after the immobilization of the CP. All potentials reported in this work are referred to the Ag/AgCl electrode.

In the first hybridization test, 5.0 µL aliquots of 200 nM of poly(AT)$_{20}$ poly(AG)$_{20}$ and poly(G)$_{40}$ in TE are hybridized with their corresponding complementary CP coated electrodes, respectively. For comparison, the same set of electrodes are treated with 5.0 µL aliquots of 200 nM of poly(T)$_{40}$. Upon hybridization, the oligonucleotides are selectively bound to their complementary CPs and become fixed on the electrode surface. Thorough rinsing with the hybridization buffer washes off all of the non-hybridization related oligonucleotides. PIND-Ru is brought to the electrode surface during a subsequent incubation with the 5.0 µl aliquot of 100 µg/ml of PIND-Ru in the hybridization solution. It is found that extensive washing with NaCl saturated 10 mM phosphate buffer containing 10% ethanol removes most of the non-DNA related PIND-Ru uptake.

Figure 6A:
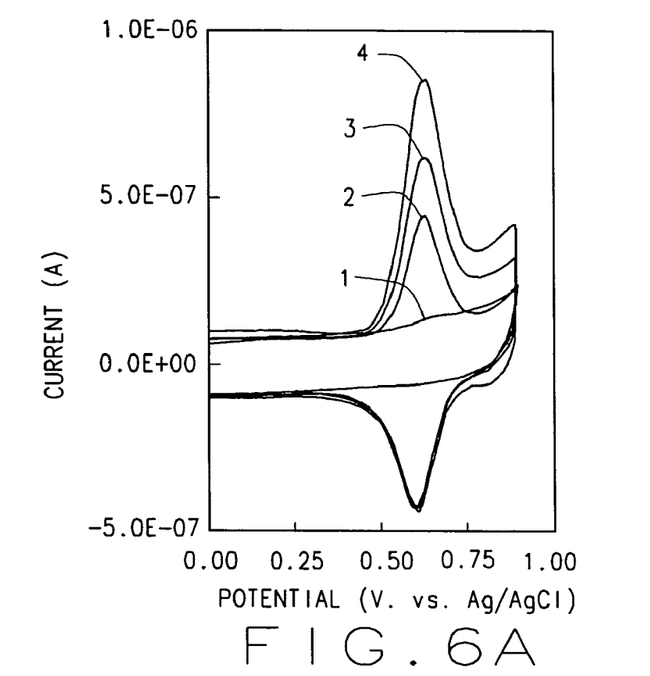

Cyclic voltammograms for the electrodes after hybridization are shown in FIG. 6A. For the non-complementary poly (T)$_{40}$, one pair of minute voltammetric peaks are observed at the redox potential of PIND-Ru (0.63 V) after hybridization (FIG. 6A trace 1), largely due to pure electrostatic interaction of PIND-Ru and CP on the electrode surface. For the complementary poly(AT)$_{20}$ poly(AG)$_{20}$ and poly(G)$_{40}$, slight positive shifts in the redox potential are observed and the peak current increases by as much as 100-fold (FIG. 6A traces 2, 3 and 4). The observed current, 0.30 µA after hybridization to 200 nM of poly(AT)$_{20}$, results therefore from 1.3 pmol of active and intercalated PIND-Ru. This number represents <0.50% of PIND-Ru contained in the assayed droplet. Taking $1.2 \times 10^{-11}$ mol/cm$^2$ (midrange of the estimated values) as the surface CP coverage and assuming that the maximum PIND-Ru/base ratio of 1/4, 0.13 pmol of the target DNA is hybridized. Thus, 13% of the target DNA and 15% of the surface-bound CP is actually hybridized, which is comparable to those found in the literature. Interestingly, when poly(AG)$_{20}$ and poly(G)$_{40}$ are hybridized with their corresponding complementary CP coated electrodes, noticeable increments in anodic current and slight decreases in cathodic current are observed (FIG. 6A traces 3 and 4), and the increment increases nearly linearly with increasing guanine content, indicating that guanines in the oligonucleotides are catalytically oxidized at 0.63 V by the intercalated PIND-Ru. These results demonstrate that PIND-Ru selectively interacts with ds-DNA and the PIND-Ru-ds-DNA adduct has a very slow dissociation rate and highly efficient electrocatalysis of guanine oxidation, which paves the way for developing an ultrasensitive DNA biosensors.

Next, the intercalated PIND-Ru, as the electroactive indicator, for direct detecting cancer susceptibility genes in mRNA is evaluated, taking the full length tumour protein p53 (TP53) gene in mRNA as our target gene. Prior to hybridization, the mRNA mixture is denatured at 70° C. for 10 min. Oligonucleotides with sequences complementary to TP53 gene are immobilized on the electrode surface and served as CP. Upon hybridization at 53° C. for 30 min, TP53 mRNA from the mixture is selectively bound to the electrode surface. Thorough rinsing with the hybridization buffer washes off all of the non-hybridization-related mRNA.

Figure 6B:
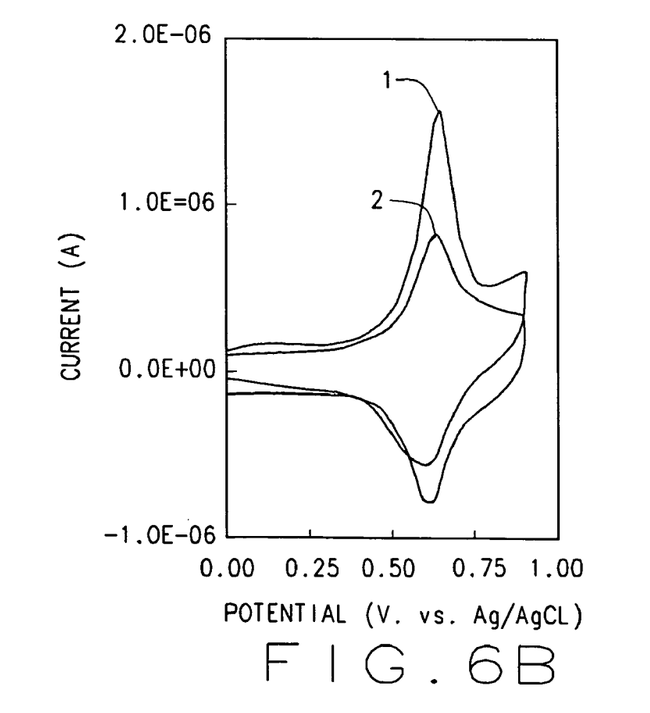

As seen in FIG. 6B, a typical cyclic voltammogram of the electrode after applying PIND-Ru, considerably higher peak current is observed for the anodic process, indicating that larger amount of electrons is involved in the oxidation process, most probably due to the captured long TP53 mRNA molecules which bring a much larger amount of guanine to the electrode surface. The peak current drops significantly during successive potential cycling and a steady-state voltammogram is attained after 5 cycles between 0 and 0.90 V (FIG. 5B trace 2). Integration of oxidation or reduction current peak at slow scan rate $\leqq 10$ mV/s yields a surface coverage of 3.8 pmol in terms of electroactive $Ru^{2+}/Ru^{3+}$ sites. The total amount of PIND-Ru, $1.9 \times 10^{-11}$ mole/cm$^2$, is equivalent to 32% of the CP being hybridized and fully intercalated. To have a better understanding of the hybridization efficiency and PIND-Ru loading level, a series of quartz crystal microbalance (QCM) measurements are carried out on TP53 after hybridization, and after PIND-Ru intercalation. The results are summarized in Table 1:

TABLE 1

QCM Data of CP coated quartz crystal resonators after hybridization to TP53 in 1.0 µg mRNA, and after PIND-Ru intercalation.

| | TP53 Hybridization | | | PIND-Ru Intercalation | | | |
|---|---|---|---|---|---|---|---|
| | | | Hybridized | | | | |
| Cp Coated Resonator | Δf (Hz) | Δm (ng) | TP53 (×10$^{15}$ mole) | Δf (Hz) | Δm (ng) | PIND-Ru Loading (×10$^{12}$ mole/cm$^2$) | PIND-Ru/Base Ratio |
| 1 | 17 | 15 | 38 | 5.4 | 4.7 | 15 | 1/14 |
| 2 | 18 | 16 | 41 | 7.4 | 6.5 | 22 | 1/11 |
| 3 | 16 | 14 | 36 | 5.5 | 5.0 | 17 | 1/12 |
| 4 | 19 | 17 | 43 | 6.9 | 6.1 | 21 | 1/12 |

As shown in Table 1, ~40 fmoles of TP53 is hybridized. This number represents ~1.6% of the surface-bound CP is actually hybridized which is much lower than those of short nucleotides (20-50-mers) reported in the literature. It is not surprising that the hybridization efficiency decreases drastically with increasing the length of the analyzed gene. In addition, the QCM experiments shows that one PIND-Ru intercalated per 11-14 bases of TP53, suggesting that some of the PIND-Ru molecules intercalated into the secondary structure of TP53, which further enhances the sensitivity of the method. PIND-Ru loading density is found to be in the range of $1.5$-$2.2 \times 10^{-11}$ mole/cm$^2$, which is in good agreement with that obtained in tests.

The dynamic range for the quantification of TP53 gene is established using purified cDNA transcribed from the mRNA of TP53 and diluted to different concentrations with TE buffer before use. For control experiments, non-complementary CPs are used in the electrode preparation. It is found that the current increases linearly with cDNA concentration from 2.5 to 350 pM with a detection limit of 1.5 pM, corresponding to 0.60 ng/ml. Taking the sample volume into consideration, as little as 7.5 attomoles of TP53 cDNA is successfully detected using the proposed method. Compared to the previous results of direct nucleic acid oxidation assays, the sensitivity of genomic nucleic acid assay is greatly improved by adopting the catalytic threading intercalator scheme of the present invention. The appeal of the non-labeling electrochemical method for the direct detection of nucleic acid is that genes from real-world sample that contain many of the redox active units (guanine and intercalated PIND-Ru) exhibit high sensitivity. The advantage of the PIND-Ru catalyzed system described here is that both guanine and PIND-Ru are oxidized at potential as low as 0.63 V where little background current exists. Moreover, genes with more guanines give more sensitive signal. The combination of the two enables picomolar detection limit and a dynamic range up to 350 pM. As various changes could be made in the above methods and compositions without departing from the scope of the present teachings, it is intended that all matter contained in the above description be interpreted as illustrative and not in a limiting sense. Unless explicitly stated to recite activities that have been done (i.e., using the past tense), illustrations and examples are not intended to be a representation that given embodiments of this present teachings have, or have not, been performed.

All references cited in this specification are hereby incorporated by reference in their entirety. The discussion of the references herein is intended merely to summarize the assertions made by their authors and no admission is made that any reference constitutes prior art relevant to patentability. Applicant reserves the right to challenge the accuracy and pertinency of the cited references.

What is claimed is:

1. A compound having the formula:

wherein $L_1$ and $L_2$ are each independently $C_1$-$C_{20}$ alkyl group substituted with an imidazolyl group, wherein each imidazolyl group of $L_1$ and $L_2$ is bonded to a transition metal compound of the formula:

wherein M is a metallic element that can form a coordinate bond to nitrogen;

R and R' are nitrogen-containing organic moieties coordinated to M at their nitrogen atoms, wherein R and R' are independently selected from the group consisting of
2,2'-bipyridyl;
2,2'-bipyridyl substituted with one or more substituents selected from the group consisting of $C_1$-$C_4$ alkyl, phenyl, and phenyl substituted with one or more $C_1$-$C_4$ alkyl groups;
1,10-phenanthrolinyl; and
1,10-phenanthrolinyl substituted with one or more substituents selected from the group consisting of $C_1$-$C_4$ alkyl, phenyl, and phenyl substituted with one or more $C_1$-$C_4$ alkyl groups;

Z is a halogen atom;

m is +1, +2, +3, +4, +5, or +6; and

X is an anion, or combination of anions, that balances m.

2. The compound as set forth in claim 1 wherein the compound is bonded to the transition metal compound with a metal to nitrogen coordinate bond.

3. The compound as set forth in claim 2 wherein M is selected from the group consisting of ruthenium, osmium, zinc, iron, rhodium, rhenium, platinum, scandium, titanium, vanadium, cadmium, magnesium, copper, cobalt, palladium, chromium, manganese, nickel, molybdenum, tungsten, and iridium, or mixtures thereof.

4. The compound as set forth in claim 2 wherein M is ruthenium.

5. The compound as set forth in claim 1 wherein $L_1$ and $L_2$ are propylimidazolyl.

6. The compound as set forth in claim 2 wherein Z is chloro or bromo.

7. The compound as set forth in claim 2 wherein R and R' are independently selected from the group consisting of 2,2'-bipyridyl, 4,4'-methyl-2,2'-bipyridyl, 4,4'-ethyl-2,2'-bipyridyl, 4,4'-phenyl-2,2'-bipyridyl, 5,5'-methyl-2,2'-bipyridyl, 5,5'-ethyl-2,2'-bipyridyl, and 5,5'-phenyl-2,2'-bipyridyl.

8. The compound as set forth in claim 7 wherein M is selected from the group consisting of ruthenium, osmium, zinc, iron, rhodium, rhenium, platinum, scandium, titanium, vanadium, cadmium, magnesium, copper, cobalt, palladium, chromium, manganese, nickel, molybdenum, tungsten, and iridium, or mixtures thereof.

9. The compound as set forth in claim 8 wherein M is ruthenium.

10. The compound as set forth in claim 7 wherein $L_1$ and $L_2$ are propylimidazolyl.

11. The compound as set forth in claim 7 wherein Z is chloro or bromo.

12. The compound as set forth in claim 7 wherein the R and R' comprises a moiety that can intercalate into double-stranded nucleic acid.

13. The compound as set forth in claim 1 wherein $L_1$ and $L_2$ are propylimidazolyl, at least one of R and R' is 2,2'-bipyridyl, M is ruthenium, and Z is chloro.

14. A compound having the formula:

15. A method for preparing an electrocatalytic intercalator, the method comprising contacting a core compound of the formula:

wherein $L_1$ and $L_2$ are each independently $C_1$-$C_{20}$ alkyl group substituted with an imidazolyl group, with a transition metal compound of the formula:

wherein M is a metallic element that can form a coordinate bond to nitrogen;

R and R' are nitrogen-containing organic moieties coordinated to M at their nitrogen atoms, wherein R and R' are independently selected from the group consisting of
2,2'-bipyridyl;

2,2'-bipyridyl substituted with one or more substituents selected from the group consisting of $C_1$-$C_4$ alkyl, phenyl, and phenyl substituted with one or more $C_1$-$C_4$ alkyl groups;

1,10-phenanthrolinyl; and 1,10-phenanthrolinyl substituted with one or more substituents selected from the group consisting of $C_1$-$C_4$ alkyl, phenyl, and phenyl substituted with one or more $C_1$-$C_4$ alkyl groups;

Z is a halogen atom;

m is +1, +2, +3, +4, +5, or +6; and

X is an anion, or combination of anions, that balances m, so as to form a metal to nitrogen coordinate bond between the core compound and the transition metal compound.

16. The method as set forth in claim 15 wherein M is selected from the group consisting of ruthenium, osmium, zinc, iron, rhodium, rhenium, platinum, scandium, titanium, vanadium, cadmium, magnesium, copper, cobalt, palladium, chromium, manganese, nickel, molybdenum, tungsten, and iridium, or mixtures thereof.

17. The method as set forth in claim 16 wherein M is ruthenium.

18. The method as set forth in claim 15 wherein $L_1$ and $L_2$ axe propylimidazolyl, 19. The method as set forth in claim 15 wherein Z is chloro or bromo.

20. The method as set forth in claim 15 wherein R and R' are independently selected from the group consisting of 2,2'-bipyridyl, 4,4'-methyl-2,2'-bipyridyl, 4,4'-ethyl-2,2'-bipyridyl, 4,4'-phenyl-2,2'-bipyridyl, 5,5'-methyl-2,2'-bipyridyl, 5,5'- ethyl-2,2'-bipyridyl, and 5,5'-phenyl-2,2'-bipyridyl.

21. The method as set forth in claim 20 wherein M is selected from the group consisting of ruthenium, osmium, zinc, iron, rhodium, rhenium, platinum, scandium, titanium, vanadium, cadmium, magnesium, copper, cobalt, palladium, chromium, manganese, nickel, molybdenum, tungsten, and iridium, or mixtures thereof.

22. The method as set forth in claim 21 wherein M is ruthenium.

23. The method as set forth in claim 20 wherein $L_1$ and $L_2$ are propylimidazolyl.

24. The method as set forth in claim 20 wherein Z is chloro or bromo.

25. The method as set forth in claim 15 wherein $L_1$ and $L_2$ are propylimidazolyl, at least one of R and R' is 2,2-bipyridyl, M is ruthenium, and Z is chloro.

26. A method for detecting a nucleic acid, the method comprising:

contacting in aqueous medium an electrocatalytic intercalator comprising a core compound of the formula:

wherein $L_1$ and $L_2$ are each independently $C_1$-$C_{20}$ alkyl group substituted with an imidazolyl group, wherein each imidazolyl group of $L_1$ and $L_2$ is bonded to a transition metal compound of the formula:

wherein M is a metallic element that can form a coordinate bond to nitrogen;

R and R' are nitrogen-containing organic moieties coordinated to M at their nitrogen atoms, wherein R and R' are independently selected from the group consisting of 2,2'-bipyridyl;

2,2'-bipyridyl substituted with one or more substituents selected from the group consisting of $C_1$-$C_4$ alkyl, phenyl, and phenyl substituted with one or more $C_1$-$C_4$ alkyl groups;

1,10-phenanthrolinyl; and 1,10-phenanthrolinyl substituted with one or more substituents selected from the group consisting of $C_1$-$C_4$ alkyl, phenyl, and phenyl substituted with one or more $C_1$-$C_4$ alkyl groups;

Z is a halogen atom;

m is +1, +2, +3, +4, +5, or +6; and

X is an anion, or combination of anions, that balances m, with a complex comprising the nucleic acid so as to intercalate the electrocatalytic intercalator into the complex; and detecting an electric current wherein the electrocatalytic intercalator oxidizes a nucleotide.

27. The method as set forth in claim 26 wherein the nucleotide is guanine.

28. The method as set forth in claim 26 wherein M is selected from the group consisting of ruthenium, osmium, zinc, iron, rhodium, rhenium, platinum, scandium, titanium, vanadium, cadmium, magnesium, copper, cobalt, palladium, chromium, manganese, nickel, molybdenum, tungsten, and iridium or mixtures thereof.

29. The method as set forth in claim 28 wherein M is ruthenium.

30. The method as set forth in claim 26 wherein $L_1$ and $L_2$ are propylimidazolyl.

31. The method as set forth in claim 26 wherein Z is chloro or bromo.

32. The method as set forth in claim 26, wherein the method further comprises:

immobilizing a probe on an electrode; and providing the nucleic acid in solution in contact with the electrode, wherein the probe and nucleic acid hybridize to each other.

33. The method as set forth in claim 26, wherein the method further comprises:

immobilizing a first member of a recognition pair on the electrode;

labeling a probe with a second member of the recognition pair;

combining the labeled probe in solution in contact with the electrode, wherein the probe and the nucleic acid hybridize to form a complex that is bound to a surface of the electrode.

34. The method as set forth in claim 26, wherein the electrocatalytic intercalator is a compound having the formula:

23

24

-continued

* * * * *

UNITED STATES PATENT AND TRADEMARK OFFICE
CERTIFICATE OF CORRECTION

PATENT NO. : 7,462,720 B2
APPLICATION NO. : 10/933023
DATED : December 9, 2008
INVENTOR(S) : Fang Xie, Hong Xie and Zhiqiang Gao Page 1 of 1

It is certified that error appears in the above-identified patent and that said Letters Patent is hereby corrected as shown below:

On the cover page, Under Field (76) "Inventors:" shown on the first page of the patent:
1. For inventor Zhiqiang Gao, please replace street name - "Verdr" with "Verde"

Column 6, line 55: delete "be" after "may"

Column 6, line 59: replace "5-car-boxymethylaniino-methyl-2-thioridine" with "5-car-boxymethylamino-methyl-2-thioridine"

Column 7, line 2: replace "2-methylthio-N-6-isopentenyladenosine" with "2-methylthio-N6-isopentenyladenosine"

Column 15, line 54: replace "60° C." with "60° C"

Column 15, line 56: replace "60° C." with "60° C" and "35° C." with "35° C"

Column 16, line 2: replace "Tex." with "TX"

Column 16, line 5: replace "Kans." with "KS"

Column 16, line 61: replace "70° C." with "70° C"

Column 16, line 64: replace "53° C." with "53° C"

Column 17, line 12: replace "≦" with "≤"

Column 17, line 43: replace "nucleotides" with "oligonucleotides"

Column 17, line 53: insert --voltammetric-- after "in"

Signed and Sealed this

Seventeenth Day of March, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,462,720 B2 Page 1 of 1
APPLICATION NO. : 10/933023
DATED : December 9, 2008
INVENTOR(S) : Fang Xie, Hong Xie and Zhiqiang Gao

It is certified that error appears in the above-identified patent and that said Letters Patent is hereby corrected as shown below:

On the Title page, Item (73) "Assignee:" should read:

(73) Assignee: Agency for Science, Technology and Research, Singapore (SG)

Signed and Sealed this

Fifteenth Day of December, 2009

David J. Kappos
*Director of the United States Patent and Trademark Office*